US007072706B2

(12) United States Patent
Baumgardner et al.

(10) Patent No.: US 7,072,706 B2
(45) Date of Patent: Jul. 4, 2006

(54) EQUILIBRATION METHOD FOR HIGH RESOLUTION IMAGING OF LUNG COMPLIANCE AND DISTRIBUTION OF FUNCTIONAL RESIDUAL CAPACITY

(75) Inventors: James Baumgardner, Milmont Park, PA (US); David Lipson, Wynnewood, PA (US); Rahim Rizi, Montgomeryville, PA (US); David Roberts, Rosemont, PA (US); Mitchell Schnall, Broomall, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 575 days.

(21) Appl. No.: 10/071,435

(22) Filed: Feb. 8, 2002

(65) Prior Publication Data

US 2003/0023162 A1    Jan. 30, 2003

Related U.S. Application Data

(60) Provisional application No. 60/267,282, filed on Feb. 8, 2001.

(51) Int. Cl.
*A61B 5/55* (2006.01)
(52) U.S. Cl. .................. 600/420; 600/529; 600/533; 600/538
(58) Field of Classification Search ............. 600/410, 600/420, 529, 533, 538
See application file for complete search history.

(56) References Cited

OTHER PUBLICATIONS

Altes, T.A., et al, "Hyperpolarized $^3$He MR Lung Ventilation Imaging in Asthmatics: Preliminary Findings," *J. Mag. Res. Imag.* 13(3):378-384 (2001).

Black, R.D., et al, "*In vivo He$^3$* MR Images of Guinea Pig Lungs," *Rad* 199(3):867-870 (1996).

Burns, C.B., et al, "Evaluation of Single Breath Helium Dilution Total Lung Capacity in Obstructive Lung Disease," *Am. Rev. Respir. Dis.* 130:580-583 (1984).

Darling, R.C., et al, "Studies on the Intrapulmonary Mixing of Gases. II. An Open Circuit Method For Measuring Residual Air," *J. Clin. Invest.* 19:609-618 (1940).

de Lange, E.E., et al, "Lung Air Spaces: MR Imaging Evaluation With Hyperpolarized$^3$ He Gas[1]," *Rad* 210(3):851-857 (1999).

(Continued)

*Primary Examiner*—Ruth S. Smith
(74) *Attorney, Agent, or Firm*—Evelyn H. McConathy; Drinker Biddle & Reath, LLP

(57) ABSTRACT

The present invention offers novel equilibration methods for very high resolution, three-dimensional imaging of imaging of lung compliance and distribution of functional residual capacity (FRC) in the lung using hyperpolarized helium-3 ($^3$He) gas (H$^3$He), and collecting local magnetic resonance image data therefrom. Using the present methods permits many functions that have been performed on a regional level for the whole lung using non-polarized helium, to be calculated for the first time from the local MRI measurements of local H$^3$He, such as measuring volume or compliance.

24 Claims, 2 Drawing Sheets

A          B

OTHER PUBLICATIONS

Dubois, A.B., et al, A Rapid Plethysmographic Method For Measuring Thoracic Gas Volume: A Comparison With Nitrogen Washout Methods For Measuring Functional Residual Capacity in Normal Subjects, *J. Clin. Invest.* 35:322-326 (1956).

Gattinoni, L., et al, "Effects of Positive End-Expiratory Pressure On Regional Distribution of Tidal Volume and Recruitment in Adult Respiratory Distress Syndrome," *Am. J. Respir. Crit. Care Med.* 151:1807-1814 (1995).

Gierada, D.S., et al, "Dynamic Echo Planar MR Imaging of Lung Ventilation With Hyperpolarized $^3$He in Normal Subjects and Patients With Severe Emphysema," *NMR Biomed.* 13(4):176-181 (2000).

Kauczor, H.U., et al, "Normal and Abnormal Pulmonary Ventilation: Visualization at Hyperpolarized He-3 MR Imaging," *Rad* 201:564-568 (1996).

Kauczor, H.U., et al, "Imaging of the Lungs Using 3He MRI: Preliminary Clinical Experience in 18 Patients With and Without Lung Disease," *J. Mag. Res. Imag.* 7:538-543 (1997).

MacFall, J.R., et al, "Human Lung Air Spaces: Potential For MR Imaging With Hyperpolarized He-3," *Rad* 200:553-558 (1996).

Meneely, G.R., et al, "A Simplified Closed Circuit Helium Dilution Method For the Determination of the Residual Volume of the Lungs," *Am. J. Med.* 28:824-831 (1960).

Middleton, H., et al, "MR Imaging With Hyperpolarized $^3$He Gas," *Mag. Res. Med.* 33:271-275 (1995).

Roberts, D.A., et al, "Detection and Localization of Pulmonary Air Leaks Using Laser-Polarized Helium-$^3$He MRI," *Mag. Res. Med.* 44:379-382 (2000).

Saha, P.K., et al, "Scale-Based Fuzzy Connected Image Segmentation: Theory, Algorithms, and Validation," *Computer Vision and Image Understanding*, 77:145-174 (2000).

Salerno, M., et al, "Dynamic Spiral MRI of Pulmonary Gas Flow Using Hyperpolarized $^3$He: Preliminary Studies in Healthy and Diseased Lungs," *Mag. Res. Med.* 46:667-677 (2001).

Saha, P.K. et al, "Optimum Image Thresholding via Class Uncertainty and Region Homogenity," *IEEE Transactions on Pattern Analysis and Machine Intelligence*, 23(7):689-706 (2001).

Udupa, J.K., et al, "Fuzzy Connectedness and Object Definition: Theory, Algorithms, and Applications in Image Segmentation," *Graphical Models and Image Processing*, 58(3):246-261 (1996).

EQUILIBRATION METHOD FOR HIGH RESOLUTION IMAGING OF LUNG COMPLIANCE AND DISTRIBUTION OF FUNCTIONAL RESIDUAL CAPACITY

REFERENCE TO RELATED APPLICATIONS

This application claims priority to No. 60/267,282 filed Feb. 8, 2001, herein incorporated in its entirety.

GOVERNMENT INTERESTS

This invention was supported in part by Grant Nos. K23 HL04486, RR02305, and R01-HL-64741 from the U.S. National Institutes of Health. The Government may have certain rights in this invention.

FIELD OF THE INVENTION

The present invention provides novel equilibration methods for imaging lung compliance and distribution of functional residual capacity (FRC) in the lung using hyperpolarized helium-3 ($H^3He$).

BACKGROUND OF THE INVENTION

Standard methods for measuring FRC and compliance for the whole lung have been known for years (Meneely et al., *Am. J. Med.* 28:824–831 (1960); Darling et al., *J. Clin. Invest.* 19:609–618 (1940); Burns et al., *Am. Rev. Respir. Dis.* 130:580–583 (1984); Dubois et al., *J. Clin. Invest.* 35:322–326 (1956)). The use of hyperpolarized noble gases, such as $^3He$, has been demonstrated to be useful in the imaging of gas distribution (ventilation) in the human lung (Middleton et al., *Mag. Res. Med.* 33:271–275 (1995); MacFall et al., *Rad.* 200:553–558 (1996); Kauczor et al., *Rad.* 201:564–568 (1996); Kauczor et al, *J. Mag. Res. Imag.* 7:538–543 (1997); Roberts et al., *Mag. Res. Med.* 44(3):379–382 (2000); Black et al., *Rad.* 199(3):867–870 (1996); de Lange et al., *Rad.* 210(3):851–857 (1999); Altes et al., *J. Mag. Res. Imag.* 13(3):378–384 (2001); Salerno et al., *Mag. Res. Med.* 46:667–677 (2001); Gierada et al., *NMR Biomed.* 13(4): 176–18 1 (2000)). However, what has not been available until the present invention, has been a method for high resolution imaging of the gas spaces in the lung, with very high contrast between the signal intensity for the gas phase compared to the tissue phase, which would permit the combined imaging of FRC distribution and lung compliance.

The only known work in this field is related to imaging only the distribution of FRC by a single group Gattinoni et al., *Am J Respir Crit Care Med* 151:1807–1814 (1995)). The Gattinoni group used high resolution computer tomography (HRCT) methods to assess the gravitational distribution of FRC in patients with adult respiratory distress syndrome (ARDS). However, that work was limited by the limitations of the HRCT method. The "images" they obtained for distribution of FRC were fairly low in resolution, and more importantly, those images were only 2-dimensional. Moreover, the HRCT technique was not, and is not, capable of rapid measurements of FRC for the whole lung.

Thus, a need has remained in the art until the present invention for a method providing rapid imaging of FRC distribution for the whole lung; true 3 dimensional imaging; and very high resolution imaging of lung volumes and pulmonary compliance.

SUMMARY OF THE INVENTION

The present invention offers novel equilibration methods for imaging lung compliance and distribution of functional residual capacity (FRC) in the lung using hyperpolarized helium-3 ($^3He$) gas ($H^3He$). The imaging of pulmonary compliance combined with measuring the distribution of FRC is accomplished in the present invention by, for the first time, adapting and extending helium dilution principles and standard pulmonary function tests established for imaging the whole lung, to the imaging of lung volumes and compliance. The use of hyperpolarized $^3He$ satisfies both of these requirements, and the present method has several advantages over the prior art. These include, but are not limited to, rapid imaging of FRC distribution for the whole lung; true 3 dimensional imaging; and very high resolution in the resulting image.

The present invention provides equilibration methods for very high resolution, three-dimensional imaging of pulmonary compliance, and also methods for very high resolution, three-dimensional imaging of distribution of functional residual capacity (FRC) in the lung, wherein in each case, the method comprises delivering a predetermined volume of hyperpolarized noble gas into the conducting airways in each ventilated region of the pulmonary system and collecting local magnetic resonance image data therefrom.

Also provided are equilibration methods for very high resolution, three-dimensional imaging of both pulmonary compliance and distribution of functional residual capacity (FRC) in the lung, wherein the method comprises delivering a predetermined volume of hyperpolarized noble gas into the conducting airways in each ventilated region of the pulmonary system and collecting local magnetic resonance image data therefrom.

In these methods provided in the present invention, the hyperpolarized noble gas is preferably hyperpolarized helium-3 gas ($H^3He$). Using inhaled hyperpolarized ($H^3He$) gas, three-dimensional MRI images are rapidly obtained. The $H^3He$ acts as a contrast agent, thereby providing unparalleled, high resolution images defining the airspaces. Because time of repetition (TR) is irrelevant to polarized gas imaging, a real-time series of images is obtainable.

The methods further comprise dividing the lung images into as many distinct voxels as imaging resolution permits. Local lung volume is calculated by dividing average signal intensity in each voxel by tracheal signal intensity. The average concentration of $H^3He$ in each voxel is determined by dividing an amount of $H^3He$ in each voxel by volume of the voxel, and calculating amount of $H^3He$ in each the voxel by multiplying concentration of $H^3He$ in the gas space of the voxel by volume of gas space in the voxel. Local FRC is determined by dividing signal intensity in the voxel by tracheal signal intensity, and then multiplying by volume of the voxel. Finally compliance of the voxel is determined by calculating pressure difference between alveolar gas inside the voxel and pleural space outside of the lung, and calculating local compliance in the voxel by dividing the volume of the voxel by transmural pressure gradient (tracheal minus esophageal pressures). The whole lung FRC is determined by summing all of the local FRC values in each voxel.

Further provided in the present invention are the very high resolution, three-dimensional images of pulmonary compliance, distribution of functional residual capacity (FRC) in the lung, or a combination thereof, produced by the foregoing methods using hyperpolarized $H^3He$ gas.

In addition, there are provided systems for producing the very high resolution, three-dimensional images of pulmonary compliance and distribution of functional residual capacity (FRC) in the lung in accordance with the foregoing methods, comprising: means for collecting and processing magnetic resonance imaging data from the hyperpolarized $H^3He$ gas-infused lung, conducting airways and ventilated regions of the lung; means for dividing the lung images into as many distinct voxels as imaging resolution permits; means for calculating local lung volume; means for calculating average amount and concentration of $H^3He$ in each voxel; and means for calculating local FRC and means for calculating compliance of the voxel and local compliance in the voxel.

Additional objects, advantages and novel features of the invention will be set forth in part in the description, examples and figures which follow, and in part will become apparent to those skilled in the art on examination of the following, or may be learned by practice of the invention.

DESCRIPTION OF THE DRAWINGS

The foregoing summary, as well as the following detailed description of the invention, will be better understood when read in conjunction with the appended drawings. For the purpose of illustrating the invention, there are shown in the drawings, certain embodiment(s), which are presently preferred. It should be understood, however, that the invention is not limited to the precise arrangements and instrumentalities shown.

DETAILED DESCRIPTION OF PREFERRED EMBODIMENTS

Figure 1:
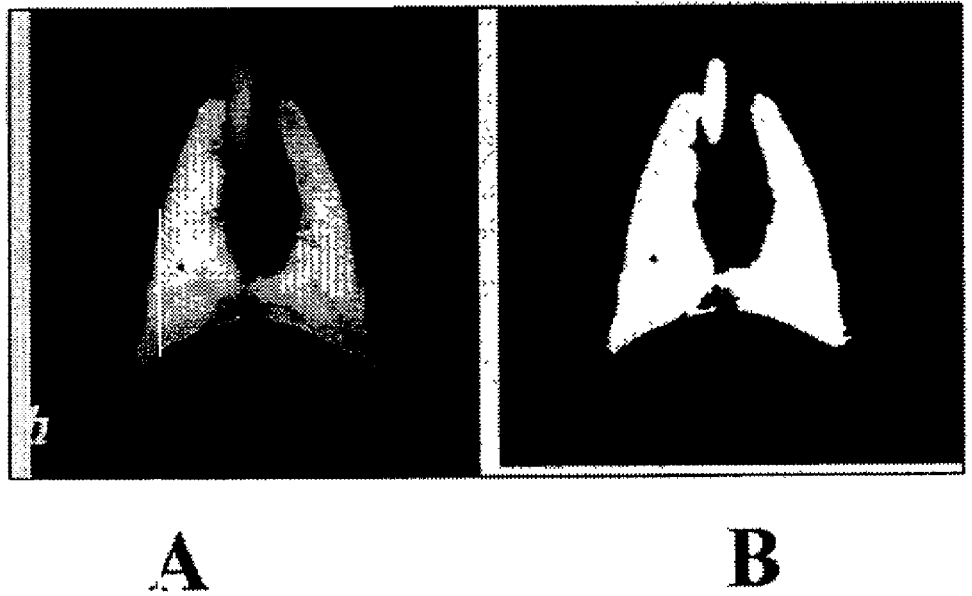
FIGS. 1A and 1B show a coronal slice of polarized $H^3He$ MR images of the lung of a normal pig (FIG. 1A) and the corresponding slice of lung volume segmentation (FIG. 1B).

Preferred embodiments of the present invention provides novel equilibration methods for imaging lung compliance and distribution of functional residual capacity (FRC) using hyperpolarized helium-3 ($H^3He$), which uses helium dilution principles to measure whole lung FRC based on well established standard pulmonary function tests. The principles of measuring whole lung volume with He are well established. However, $H^3He$-based imaging is intrinsically faster and gives much higher resolution in 3-D than other prior methods, such as computer tomography. MRI measures the local $H^3He$ concentrations at high resolution, and because $H^3He$ behaves physiologically just like regular He, the local measurements of $H^3He$ can be used to do many of the same things on a regional level that have been done with regular He for the whole lung, such as measuring volume. Consequently, the use of local measurement of $H^3He$ to measure local lung volume produces entirely novel information.

In practice, the lung is first inflated to the desired airway pressure and the endotracheal tube is then sealed, or in the case of human patients, the breath is held to fix the lung volume. Next, a known volume of $H^3He$ is introduced into the sealed or fixed lung volume and the $H^3He$ is mixed with the volume of air in the sealed lung. After adequate mixing, the lung is imaged with a homogeneous coil.

The lung images are then divided into as many distinct voxels as the imaging resolution permits, and the starting point for calculating local lung volume is the average signal intensity in each voxel divided by the signal intensity in the trachea. Neglected from the calculation are: (1) any signal decay due to oxygen or wall interactions; (2) any loss of helium from the gas spaces due to absorption by tissue or blood; and (3) any contribution to the signal from the tissue space within the voxel. The average concentration of $H^3He$ in each voxel is calculated in terms of the amount of $H^3He$ in each voxel divided by the volume of the voxel. The amount of $H^3He$ in the voxel is simply calculated in terms of the concentration of $H^3He$ in the gas space of the voxel multiplied by the volume of the gas space in the voxel. Assuming complete equilibration of the $H^3He$ throughout the lung, the concentration of $H^3He$ in the gas space of the voxel is exactly equal to the concentration of $H^3He$ in the trachea. Consequently, the average concentration of $H^3He$ in each voxel is provided by calculating:

$$\text{Conc of } H^3He = \frac{(\text{Conc of } H^3He \text{ in the trachea}) \times (\text{voxel gas volume})}{\text{voxel volume}} \quad \text{(Formula 1)}$$

Further, assuming that signal intensity is directly proportional to the concentration of $H^3He$, the gas volume ($V_g$) of each voxel is determined by calculating:

$$V_g = (S_{vox}/S_{trach}) \times V_{vox} \quad \text{(Formula 2)}$$

wherein $S_{vox}$ and $S_{trach}$ are signal intensities in the voxel and trachea, respectively, and $V_{vox}$ is the volume of the voxel.

At the end of expiration (or at a tracheal pressure of zero), local lung volume is actually also the local FRC. Therefore, local FRC is quite simply calculated as the ratio of signal intensity in the voxel divided by signal intensity in the trachea, multiplied by the volume of the voxel (Formula 2).

To calculate the compliance of the voxel, the pressure difference between the alveolar gas inside the voxel and pleural space outside of the lung must be determined. In breath-holding conditions, the alveolar pressure must equal the tracheal pressure, which is easily measured. Also during breath-hold, the pleural pressure will be nearly uniform (with a slight correction for the gravitational field), and can be estimated by measuring the esophageal pressure. The local compliance in the voxel is then simply calculated from the volume of the voxel ($V_{vox}$) divided by the transmural pressure gradient (tracheal minus esophageal pressure).

While small amounts of shunting (e.g., to the bronchial vessels) and dead-space (e.g., in the nasopharyx) are normal, a significant number of pathological pulmonary conditions are characterized by such unventilated areas. For example, blocked or impaired blood flow to an alveolus because of injury or disease, results in wasted ventilation or dead-space. However, because the volume of inspired $H^3He$ is larger than dead-space volume in the lung and related tissues, the $H^3He$ fills all of the conducting airways. In addition, a small volume of the $H^3He$ is delivered to each ventilated region of the lung.

The subject of the present method is a mammal, either breathing or not. Preferably, the mammalian subject is human. The lung(s) of such subject may be either normal for mapping purposes, or injured or diseased for therapeutic or diagnostic purposes. Both halves of the subject's lung need not be in the same condition, and may be compared against each other. Alternatively, a normal lung may also be used for comparison purposes.

MRI imaging with $H^3He$ is ideal for the three requirements of the preferred embodiment of the methods of the present invention—high resolution, high signal intensity, and rapid time resolution. Commercially available MRI systems, such as those manufactured by GE and Siemens, and improvements thereof are well known in the art, and may be used and adapted for these methods.

EXAMPLES

The present invention is further described in the following examples. These examples are not to be construed as limiting the scope of the appended claims.

Example 1

Images of FRC Distribution and Lung Compliance in Animal Models

Confirming the feasibility and effectiveness of the disclosed method, preliminary data were collected using high-resolution images of $H^3He$ distribution in the nitrogen inflated lungs of sacrificed pigs.

After sedation, Yorkshire pigs (25–30 kg; n=5) were intubated, and mechanical ventilation under isoflurane general anesthesia was maintained. Invasive lines were placed, and the animal was transported to the MRI scanner. For imaging airspaces, $H^3He$ was produced by the optical pumping spin-exchange technique. An efficient and compact gradient-echo pulse sequence with the following imaging parameters was used: TE/TR=0.8/2.8 msec, matrix=128×128×10. The $H^3He$ ventilation images of the pig lung appeared homogeneous and uniform throughout the lungs (FIGS. 1A and 1B), making the image processing task much easier, and hence, more robust.

The lung volume was measured by segmenting the lung using scale-based fuzzy connectedness (see, e.g., Udupa et al., *Graphical Models and Image Processing*, 58:246–261 (1996); Saha et al., *Computer Vision and Image Understanding*, 77:145–174 (2000)). Scale-based fuzzy connectedness is a region-growing technique starting from seed points specified in the core of the lung. Scale is described as a local morphometric parameter, and is defined at an image point p as the radius of the largest hyperball inside a homogenous region with center at p. A hard segmentation of the fuzzy lung image was obtained by using a optimal threshholding method (Udupa et al., *IEEE Transactions on Pattern Analysis and Machine Intelligence*, 23:689–706 (2001)) that selected the threshold that best complied with object morphology.

Scale-based fuzzy segmentation of the ventilation images generated an image that assigned high membership values to lung tissue regions, and low values to non lung regions. The optimum threshold selection method generated hard segmentations from the fuzzy lung images that were visually acceptable for all cases. The lung volume was calculated from each segmentation.

Figure 2:
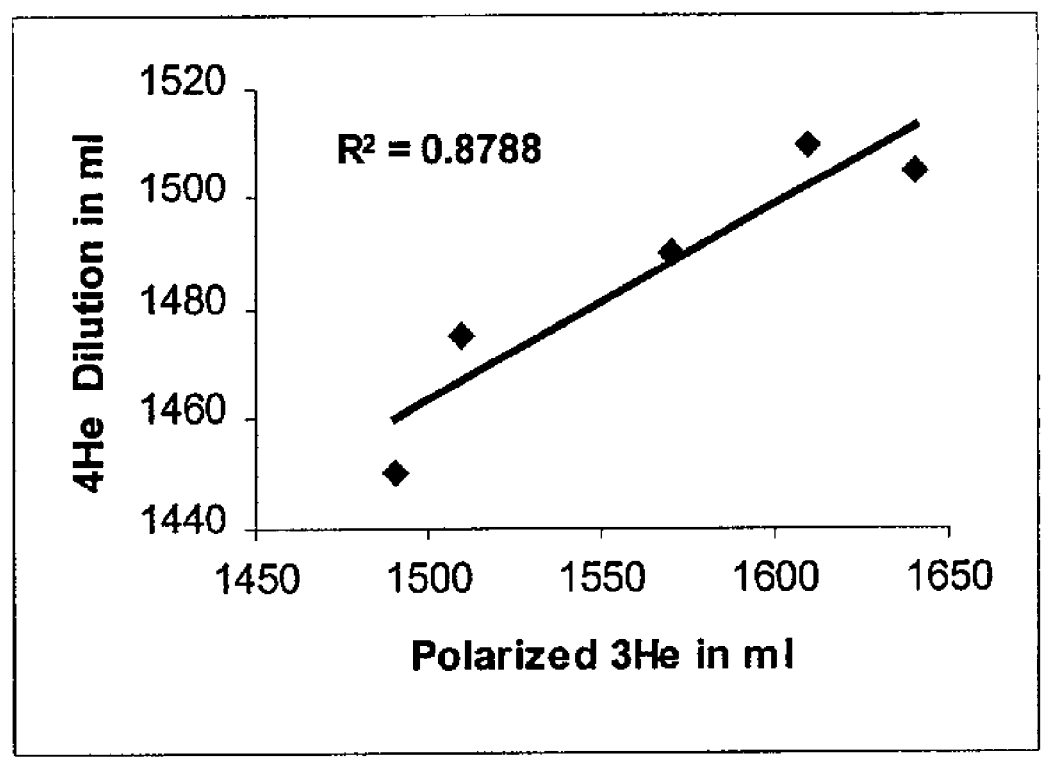
FIG. 2 graphically depicts the correlation between lung volumes measured using the proposed method and those using $^4He$ dilution technique. X axis=lung volume (in ml), calculated using the method of the present invention. Y axis=same measurements using $^4He$ dilution technique. Based on linear coefficient, the $R^2$=0.88 value shows acceptable agreement.

To validate the results produced by this method, $^4He$ dilution techniques were used and the total volume of the lung was measured for each case. The lung volumes obtained using the two methods were compared, as shown in FIG. 2. As shown, the x axis depicts the lung volume (in ml), calculated using the method of the present invention; the y axis depicts the same measurements using previously validated $^4He$ dilution techniques. A linear correlation coefficient was computed for this data, and the $R^2=0.88$ value shows an acceptable agreement.

When summed, the measurements of regional lung volumes equal standard measurements of whole lung volumes. As a result, this calculation validates the techniques used in the present example against a known benchmark. This was necessary because there is no established technique to validate measurements of regional lung volumes. (There are only techniques known for measuring whole lung volumes).

To further reduce this technique to practice (1) the images of $H^3He$ distribution are converted into images of FRC distribution and images of lung compliance, and the sum of local FRC measurements are compared to whole lung FRC measured by standard $^4He$ dilution; (2) the same experiments are repeated in the lungs of live animals in the presence of oxygen, and corrected for signal decay in oxygen to show that the corrected images of FRC distribution and compliance matched those obtained in the lungs of a comparable pig without oxygen; (3) for comparison a unilateral injury will be inflicted on one lung of the test animal, thereby reducing compliance in that lung in a predictable way, then it can be determined whether the measured local changes in compliance match the predicted changes. Although correction of $O_2$ decay is not a standard practice in imaging FRC distribution and compliance, it was necessary in applying the methods of the present invention because in live subjects lung compliance changes (decreases) in connection with various injury states, such as ARDS and pneumothorax.

Because there have been no prior reported methods for imaging FRC or compliance, there are no existing standards available for direct comparison to the equilibration method. However, whole lung FRC is readily measured by standard helium dilution techniques, and the sum of all the individual FRC in each voxel is equal to that of the whole lung FRC, providing a basis for comparison with prior methods.

Example 2

Single Breath/Pause Method for Measuring Distribution of Tidal Volume and for Imaging Lung Compliance The single breath/pause method is also a technique for imaging lung compliance, and for measuring distributions of tidal volume throughout the lungs. In all subjects there were no apparent adverse effects from inhalation of the hyperpolarized helium gas. Blood pressure and oxygen saturation was continuously measured in the patients throughout the experiments.

In the single breath/pause method, a single breath of $H^3He$ is delivered in early inspiration in a volume that exceeds dead-space volume of the lung, and then inspiration is stopped with a breath-hold. Because the volume of inspired $H^3He$ is larger than dead-space volume, the $H^3He$ fills all of the conducting airways. In addition, a small volume of the $H^3He$ is delivered to each ventilated region of the lung. Images of the $H^3He$ are obtained immediately while the breath is held.

Magnetic resonance data were acquired at the MR imaging (MRI) center of the Hospital of the University of Pennsylvania using a superconducting 1.5 Tesla imaging system equipped with high-powered gradients (Echospeed Signa, 5.6 revision software, GE Medical Systems, Milwaukee, Wis.). Proton imaging was performed at 63.8 MHz using a standard birdcage body coil for both signal transmission and reception. Helium imaging was performed at 48.65 MHz using a custom-built, broadband 26 cm diameter octagonal transmit/receive surface coil placed on the anterior thorax.

Pulmonary ventilation imaging was performed using hyperpolarized $^3$He (H$^3$He). The hyperpolarized gas was prepared through spin-exchange collisions with optically-pumped laser rubidium atoms. (Colegrove et al., *Phys. Rev.* 132:2561–2572 (1963); Gentile et al., *Phys. Rev. A.* 47:456–467 (1993); Happer et al., *Phys. Rev. A.* 29: 3092–3110 (1984); Ebert et al., *Lancet* 347:1297–1299 (1996); Saam, *Nat. Med.* 2:358–359 (1996)). Polarization levels of 5%–15% were achieved. After polarization, the gas was transferred to the animal subject while the patient/subject was lying in a supine position in the MRI magnet device. The subjects inhaled approximately 15 cc/kg of the H$^3$He gas to near total lung capacity (TLC).

To ensure that sufficient magnetization would be left after all radiofrequency (RF) pulses used in the imaging pulse sequence, a nominal constant flip angle of 12° was applied. The repetition time (TR) was selected to be as short as possible as to reduce depolarization due to the presence of O$_2$. The echo-time (TE) was also chosen to be as short as possible in order to minimize unwanted echo attenuation due to the high diffusion of the noble gas. The imaging parameters were as follows: TR=18 minutes, TE=3 minutes, matrix size 256×128, field-of-view (FOV)=40×40 cm, slice thickness=7 mm, and number of slices=6. The voxel resolution was 1.5×3×7 mm.

As above, the lung is divided into as many distinct voxels as the imaging resolution permits. In each voxel, the amount of H$^3$He that enters the voxel is diluted into the gas already present in that region of the lung. As described above, the average concentration of H$^3$He in the voxel is the total amount of H$^3$He in the voxel, divided by the voxel volume V$_{vox}$. The total amount of H$^3$He in the voxel is provided by the concentration of H$^3$He in the inspired gas, C$_g$, multiplied by the volume of the H$^3$He that entered the voxel, V$_g$. Again, assuming that signal intensity is directly proportional to the concentration of H$^3$He, the volume of the inspired H$^3$He that entered the voxel is represented by Formula 2 (V$_g$=(S$_{vox}$/S$_{trach}$)×V$_{vox}$).

A very simple expression relates the amount of tidal volume entering each voxel to the voxel volume multiplied by the ratio of voxel signal intensity to signal intensity in the trachea. To calculate local compliance from this distribution of tidal volume, required determining the pressure differential between the inside and the outside of the lung, which was equal to tracheal pressure minus esophageal pressure. This is because at the end of the breath-hold, alveolar pressure must equal tracheal pressure, and pleural pressure must be nearly uniform.

Very high-resolution images of the gas spaces, with very high contrast between the gas phase signal and the tissue signal are produced of the inflated lung to permit the greatest possible number of voxels to be acquired. This method permits images to be acquired with very rapid time resolution, which is essential since the images must be acquired immediately after initiation of the breath-hold to avoid diffusive mixing of the H$^3$He in the airways. Although presently generated in the absence of oxygen, the volume measurements have been validated.

Example 3

The Dynamic Single Breath Method for Imaging Local Ventilation

This method is an extension of the single breath/pause method, in which rapid, sequential images of image intensity are obtained in each voxel throughout inspiration as a single breath of H$^3$He is inhaled. Each image in the sequence is analyzed according to the signal intensity divided by the product of the signal intensity in the trachea multiplied by the voxel volume. This calculation provides the volume of inhaled gas entering each voxel as a function of time, and provides a high-resolution image of local ventilation.

In sum, it is feasible to obtain in vivo total lung capacity measurements and regional lung volumes by H$^3$He MRI thereby providing a functional lung imaging method, which adds potential quantitative information for assessment and management of patients with lung diseases.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

We claim:

1. An equilibration method for very high resolution, three-dimensional imaging and determination of pulmonary compliance, wherein the method comprises:

delivering and distributing a predetermined volume of hyperpolarized noble gas to conducting airways in each ventilated lung region of a pulmonary system, wherein the lung is inflated and sealed, or during a lung-inflating held breath (tidal volume);

measuring distributed volume of local concentrations of the hyperpolarized noble gas in the airways by high resolution, three-dimensional local magnetic resonance imaging, wherein the lung image is segmented using scale-based fuzzy connectedness; and calculating local pulmonary compliance from said imaged distribution.

2. The method of claim 1, wherein the noble gas is hyperpolarized helium-3 gas (H$^3$He).

3. The method of claim 2, further comprising dividing the lung images into as many distinct voxels as imaging resolution permits.

4. The method of claim 3, further comprising calculating local lung volume by dividing average signal intensity in each voxel by tracheal signal intensity.

5. The method of claim 4, further comprising calculating average concentration of H$^3$He in each voxel by dividing an amount of H$^3$He in each voxel by volume of the voxel, and calculating amount of H$^3$He in each voxel by multiplying concentration of H$^3$He in the gas space of the voxel by volume of gas space in the voxel.

6. The method of claim 5, further comprising calculating compliance of the voxel by calculating pressure difference between alveolar gas inside the voxel and pleural space outside of the lung, and calculating local compliance in the voxel by dividing the volume of the voxel by transmural pressure gradient (tracheal minus esophageal pressures).

7. An equilibration method for very high resolution, three-dimensional imaging and determination of lung functional residual capacity (FRC) using hyperpolarized noble gas, wherein the method comprises:
   delivering and distributing a predetermined volume of hyperpolarized noble gas to conducting airways in each ventilated lung region of a pulmonary system;
   measuring distributed volume of local concentrations of the hyperpolarized noble gas to provide local FRC by high resolution, three-dimensional local magnetic resonance imaging, wherein the lung image is segmented using scale-based fuzzy connectedness; and
   determining whole lung FRC based upon summation of the local FRC measurements.

8. The method of claim 7, wherein the noble gas is hyperpolarized helium-3 gas ($H^3He$).

9. The method of claim 8, further comprising dividing the lung images into as many distinct voxels as imaging resolution permits.

10. The method of claim 9, further comprising, calculating local lung volume by dividing average signal intensity in each voxel by tracheal signal intensity.

11. The method of claim 10, further comprising calculating average concentration of $H^3He$ in each voxel by dividing an amount of $H^3He$ in each voxel by volume of the voxel, and calculating amount of $H^3He$ in each voxel by multiplying concentration of $H^3He$ in the gas space of the voxel by volume of gas space in the voxel.

12. The method of claim 11, further comprising calculating local FRC by dividing signal intensity in the voxel by tracheal signal intensity, and then multiplying by volume of the voxel.

13. The method of claim 12, further comprising summing all local FRC from each voxel to determine whole lung FRC.

14. An equilibration method for very high resolution, three-dimensional imaging and determination of pulmonary compliance and distribution of lung functional residual capacity (FRC) using hyperpolarized noble gas, wherein the method comprises:
   delivering and distributing a predetermined volume of hyperpolarized noble gas to conducting airways in each ventilated region of a pulmonary system, wherein the lung is inflated and sealed, or during a lung-inflating held breath (tidal volume);
   measuring distributed volume of local concentrations of the hyperpolarized noble gas in the airways by high resolution, three-dimensional local magnetic resonance imaging and local FRC, wherein the lung image is segmented using scale-based fuzzy connectedness;
   calculating local pulmonary compliance from said measured distribution; and
   determining whole lung FRC based upon summation of the local FRC measurements.

15. The method of claim 14, wherein the noble gas is hyperpolarized helium-3 gas ($H^3He$).

16. The method of claim 15, further comprising dividing the lung images into as many distinct voxels as imaging resolution permits.

17. The method of claim 16, further comprising calculating local lung volume by dividing average signal intensity in each voxel by tracheal signal intensity.

18. The method of claim 17, further comprising calculating average concentration of $H^3He$ in each voxel by dividing an amount of $H^3He$ in each voxel by volume of the voxel, and calculating amount of $H^3He$ in each voxel by multiplying concentration of $H^3He$ in the gas space of the voxel by volume of gas space in the voxel.

19. The method of claim 18, further comprising calculating local FRC by dividing signal intensity in the voxel by tracheal signal intensity, and then multiplying by volume of the voxel.

20. The method of claim 19, further comprising calculating compliance of the voxel by calculating pressure difference between alveolar gas inside the voxel and pleural space outside of the lung, and calculating local compliance in the voxel by dividing the volume of the voxel by transmural pressure gradient (tracheal minus esophageal pressures).

21. The method of claim 15, wherein the method for very high resolution, three-dimensional imaging of pulmonary compliance and distribution of functional residual capacity (FRC) in the lung using $H^3He$ is applied to the pulmonary system of a mammalian subject.

22. The method of claim 21, wherein the mammalian subject is human.

23. The method of claim 21, wherein the lung is normal.

24. The method of claim 21, wherein the lung is injured or diseased.

* * * * *